United States Patent [19]
Lee

[11] Patent Number: 5,251,619
[45] Date of Patent: Oct. 12, 1993

[54] TONOMETRIC TRACHEAL TUBE

[76] Inventor: Myung-Ho Lee, 21 E. Hillside Terrace Ave., White Plains, N.Y. 10601

[21] Appl. No.: 802,359

[22] Filed: Dec. 4, 1991

[51] Int. Cl.$^5$ .................... A61M 16/04; A61B 5/02
[52] U.S. Cl. .................... 128/207.15; 128/207.14; 128/635
[58] Field of Search ............... 128/207.14, 207.15, 128/207.16, 207.17, 911, 633, 635, 760, 767, 769

[56] References Cited

U.S. PATENT DOCUMENTS

| | | | |
|---|---|---|---|
| 3,173,418 | 3/1965 | Baran | 128/207.15 |
| 3,854,484 | 12/1974 | Jackson | 128/207.14 X |
| 4,643,192 | 2/1987 | Fiddian-Green | 128/632 |
| 4,791,923 | 12/1988 | Shapiro | 128/207.15 |
| 5,033,466 | 7/1991 | Weymuller, Jr. | 128/207.14 X |

FOREIGN PATENT DOCUMENTS

| | | | |
|---|---|---|---|
| 1069826 | 1/1984 | U.S.S.R. | 128/207.15 |
| 90/01894 | 3/1990 | World Int. Prop. O. | 128/635 |

OTHER PUBLICATIONS

Kivissan; J., Ninikoski; J., Use of Silastic Tube and Capillary Sampling Technic in the Measurement of Tissue PO$_2$ and PCO$_2$, Am J. Surg. 125: pp. 623-627, 1973.

Dobrin; P., Canfield; T.: Cuffed Endotracheal Tubes: Mucosal Pressures and Tracheal Wall Blood Flow, Am. J. Surg. 133: pp. 562-568, 1977.

Goldberg; M., Pearson; F. G.: Pathogenesis of Trachel Stenosis following Tracheostomy with a cuffed tube, Thorax 27: pp. 678-691.

Lee; M. H., Gastric Mucosal pH as a prognostic index of mortality in critically ill patients, (In press) Crt Care Med., 1992.

Primary Examiner—V. Millin
Assistant Examiner—Raleigh W. Chiu

[57] ABSTRACT

A tracheal tube for artificial ventilation employs a primary sealant cuff and a tonometry cuff for monitoring the degree of local tracheal mucosal ischemia resulting from the pressure exerted by the primary cuff. The tonometry cuff employs a balloon sleeve of silicone elastomer membrane which is permeable to free gas but not liquid. The tonometry cuff is located on the primary sealant cuff so that during tonometry it is in full contact with the tracheal wall under the pressure of the primary cuff. The tonometry balloon sleeve is sealed against the primary cuff in a reverse folded configuration. The tube wall includes a number of lumens which may be employed for various auxiliary functions.

2 Claims, 3 Drawing Sheets

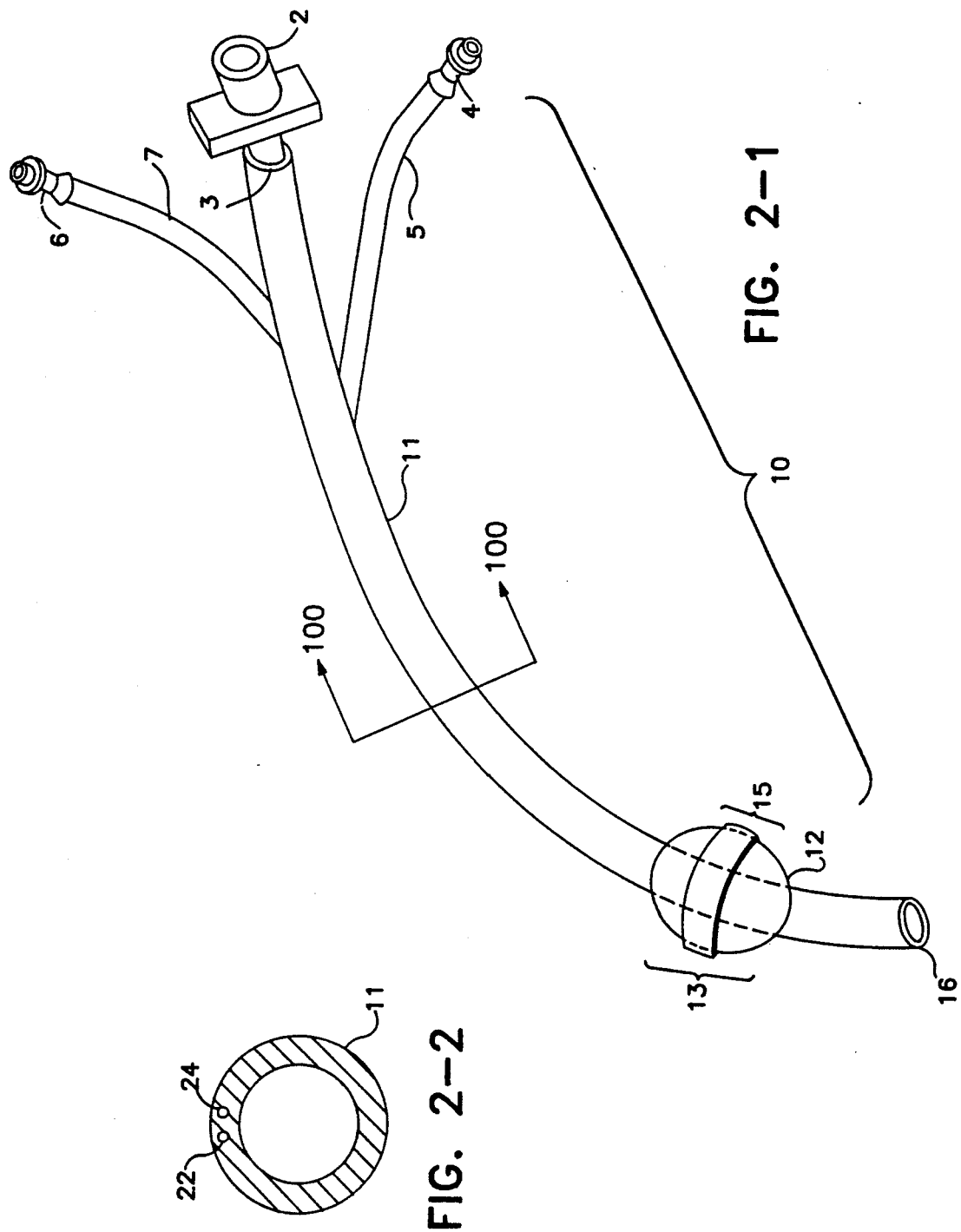

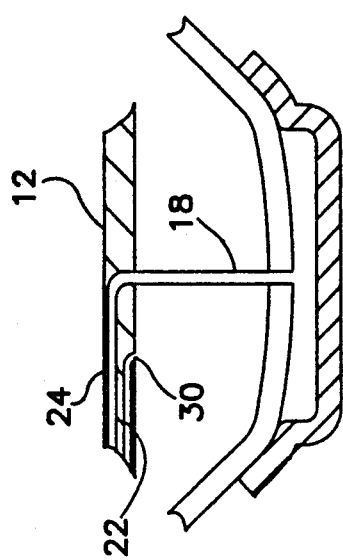
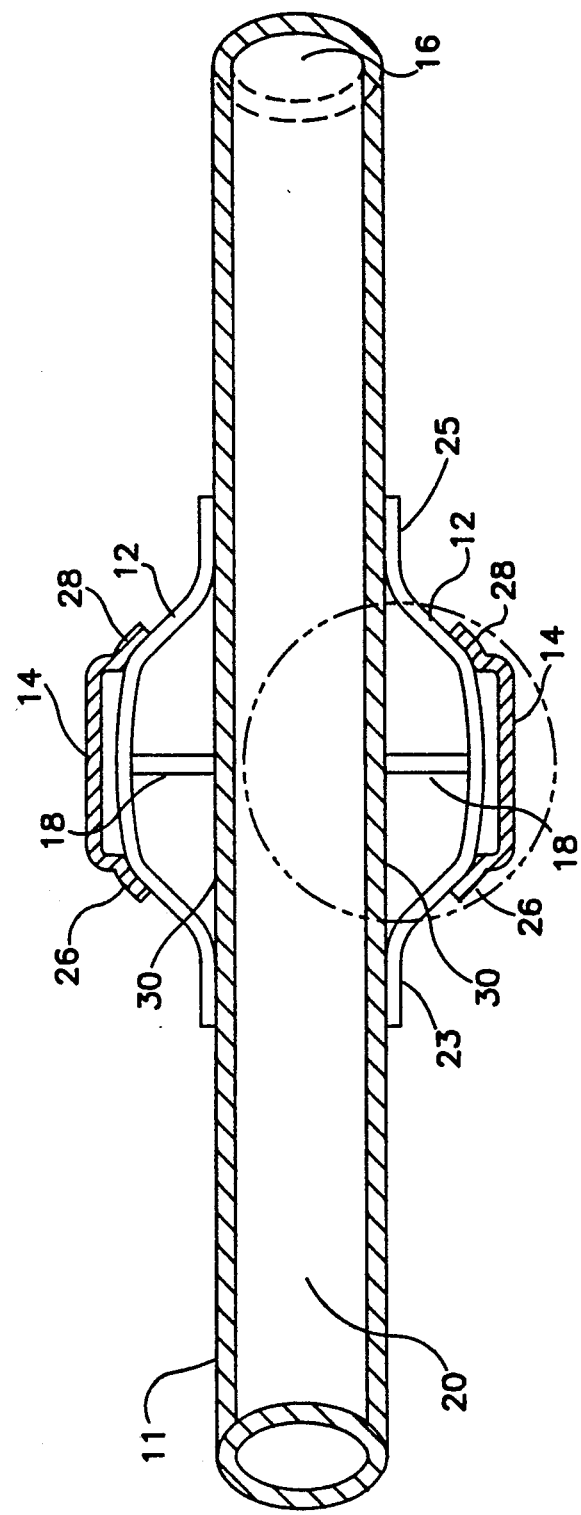

1

TONOMETRIC TRACHEAL TUBE

FIELD OF THE INVENTION

Generally, this invention relates to medical instrument and methods in medical treatments. More specifically, the invention includes an improved cuffed tracheal tubes and methods to monitor the degree of ischemia of the tracheal wall under the inflated cuff.

BACKGROUND OF THE INVENTION

Cuffed endotracheal and tracheostomy tubes are invaluable for maintaining ventilation in the management of the critically-ill patients. These tubes are sealed in the tracheal or bronchial lumen by inflating a balloon-like cuff which surrounds the airway tube. The cuff permits maintenance of airway pressures during mechanical inflation of the lungs by the respirator, and also prevents aspiration of the regurgitated gastro-esophageal contents. However, a hazard caused by the use of the device is the damage inflicted to the tracheal or bronchial wall by the inflated cuff.

The most common complications include loss of mucosal cilia, ulceration, hemorrhage, tracheal or bronchial stenosis, tracheoesophageal fistula and tracheal dilation. All of these complications are considered to result from the pressure exerted against the tracheal or bronchial mucosa by the inflated cuff, resulting in impaired local perfusion and ischemia of the site under the cuff. Currently there is no established method of bedside evaluation of this mucosal injury except intermittent endoscopic examination of the cuff site. However, this is an invasive procedure, and there could be inter- and intra-observer variations. This may not detect the early injury which could be reversible by simple management, such as simply decreasing the intra-cuff pressure by removing small amount of air from the cuff. Also this procedure may require transient deflation of the cuff to visualize the area under the cuff, which could cause aspiration of gastric regurgitant.

To overcome these problems, it is essential to review the pathophysiology of tracheal injury at the cuff site. It is generally accepted that the nature of tracheal injury is ischemic, resulting from low perfusion by cuff pressure. Thus, to monitor the injury of the tracheal wall at the cuff site, it is reasonable to follow the degree of ischemia at the inflicted tracheal wall. For better understanding of the pathophysiology of tissue ischemia of hypoperfusion, it is essential to review the acid-base buffer system of cells.

In normal physiologic condition, there is carbonic acid/bicarbonate buffer system in equilibrium with hydrogen ion as in equation I.

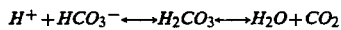
$$H^+ + HCO_3^- \longleftrightarrow H_2CO_3 \longleftrightarrow H_2O + CO_2 \qquad (I)$$

When hydrogen ion is increased by any cellular metabolism or insults, the reaction will proceed toward the right in equation I. Then it will result in decreased level of bicarbonate, increased production of carbon dioxide to buffer the increase of hydrogen ion level. Finally, the elevation of carbon dioxide will be lowered by rapid diffusion of carbon dioxide across the cell membrane to venous blood, where it will be transfered to central ventilation system. In tissue hypoxia of low perfusion, intracellular hydrogen ion level is increased by anaerobic metabolism or hydrolysis of ATP. Also, because of low perfusion, carbon dioxide will not be lowered well enough. As a result, intracellular hydrogen ion level will remained high without being buffered well enough, futher causing metabolic derangement.

Let's assume that in the equilibrium state of normal perfusion, hydrogen is $A1(nEq/L)$, bicarbonate level $B1(mEq/L)$, carbonic acid level $C1(m\ mol/L)$, partial pressure of carbon dioxide $D1(mm\ Hg)$, and the volume of the solution is $Q(Liter)$. Here, let's suppose that certain amount ($p\ m\ mol$) of hydrogen ion is added and carbon dioxide is not going to be cleared out of the system as in tissue hypoperfusion. If the concentration of hydrogen ion, bicarbonate, carbonic acid, and partial pressure of carbon dioxide is $A2, B2, C2$ and $D2$ respectively, then $$(C2) \cdot Q = (C1) \cdot Q + P \qquad (II)$$

Since the solubility coefficient for carbon dioxide is 0.0301 m mol/L/mm Hg, $$C1 = (0.0301) \cdot D1 \qquad (III)$$

$$C2 = (0.0301) \cdot D2 \qquad (IV)$$

The following can be easily derived from equation II, III and IV.

$$P/Q = (0.0301) \cdot (D2 - D1) \qquad (V)$$

It has been well known that tissue ischemia secondary to low perfusion is characterized by increased production of hydrogen ion, carbon dioxide in the cells and insufficient transfer of the carbon dioxide out of the component cells. Therefore it is reasonable to follow the hydrogen ion and carbon dioxide levels to monitor the degree of the ischemia of a tissue. That is, the extent of hydrogen ion level added in the cell can represent the degree of insults caused by hypoperfusion.

By equation (V), the amount of added hydrogen ion can be estimated by monitoring the carbon dioxide level in normal($D1$) and hypoperfusion($D2$) state. Since carbon dioxide diffuses freely, intracellular carbon dioxide level in normal cells is considered equal to that of arterial blood. Free gas can penetrate silicone membrane easily, but not liquid. Thus, carbon dioxide level in the under-perfused cells can be estimated by implanting a silicone membrane chamber into the target tissue. The chamber is then perfused with saline that equilibrates to the average carbon dioxide of the surrounding tissue medium.

The measurement of carbon dioxide of tissue has been tried in soft tissue, bone, and gastrointestinal tract. In gastrointestinal tonometry, Fiddian-Green introduced the concept of tonometric pHi, which was derived by Henderson-Hasselbalch equation. However, arterial bicarbonate was used for calculation instead of intracellular level. Therefore it is not clear at present what the pHi indicates clinically, even though there are several reports that it correlates well to intracellular pH measured directly. In one animal experiment, the pHi does not correlate well especially when actual wall pH of the intestine becomes lower ranges(underperfused state). Therefore, apparently it is more physiologic to follow arterial and tonometrically-derived carbon dioxide level rather than ambiguously-defined pHi.

Accordingly, this invention is directed to provide an instrument and a method for monitoring the degree of tracheal wall injury caused by the inflated cuff pressure during mechanical ventilation.

SUMMARY AND OBJECTIVE OF THE INVENTION

Briefly, the invention, in a preferred form but not limited to, is an improved cuffed tracheal tube(endotracheal or tracheostomy tube) which has a chamber at and on the cuff site, measuring the intramucosal partial pressure of the carbon dioxide of the trachea which is under the pressure of the inflated cuff.

The tube comprises a main hollow tubular member for ventilation passage which extends between a proximal and a distal end. An inflatable primary sealant sleeve encircles the tube between the proximal and distal ends for sealing the tube against the tracheal or bronchial wall upon inflation of the sleeve. A second sleeve is located on the primary sealant cuff. The second sleeve is composed of particular material that is permeable to free gas but not liquid contents of the tracheo-bronchial wall. A manually operable device, for selectively inflating and deflating the primary sleeve, communicates through a first lumen which is formed in the wall of the main tubular member to convey the requisite pressurized fluid or gas to the sleeve. The second manually operable device communicates through a second lumen, which extends longitudinally in the wall of the main tubular member, with the second sleeve. Liquid, suitably normal saline, can be placed into or withdrawn from the inside of the sleeve via the second lumen. The tubular wall also may have single primary cuffs as described, or plural primary cuffs with single or plural second sleeve. Tube wall may also have a plurality of additional lumens for suctioning purpose, for monitoring various functions and introducing substances.

For operation of the device, the primary sealant cuff is inflated first after the placement of the tracheal tube at the proper position. For the tonometry of the tracheal wall under the inflated primary cuff, certain amount of testing liquid, preferably normal saline, is filled into the tonometric cuff and the same amount of air will be removed from the primary cuff. This will maintain the pressure exerted on the tracheal wall by the cuffs during the mechanical ventilation of the lungs and also prevent the air leakage from the airway passage. After a certain period, preferably 30 minutes, the saline is withdrawn from the tonometric cuff and is subjected to regular blood gas analyzer to obtain the carbon dioxide level. The same amount of the air should be added to the primary sealant cuff as soon as the saline is wathdrawn from the tonometry cuff. Arterial carbon dioxide level should be obtained at the time of the tonometry.

An object of the invention is to provide a new and improved tracheal(endotracheal or tracheostomy) tube.

Other object of the invention is to measure the intramucosal partial pressure of carbon dioxide of the tracheal wall under the inflated cuff.

Other object of the invention is the measuring the degree of the ischemic injury of the tracheal wall under the inflated cuff pressure.

Other objects and advantages of the invention will become apparent from the drawings and specifications.

BRIEF DESCRIPTION OF THE DRAWINGS

FIG. 2-1 is an enlarged perspective view of the endotracheal tube of the present invention.

FIG. 2-2 is a cross-sectional view taken along lines A—A of FIG. 2, showing intramural lumen of the endotracheal tube.

FIG. 3-1 is a cross-sectional view taken along the longitudinal axis adjacent the distal end of the assembly.

Figure 1:
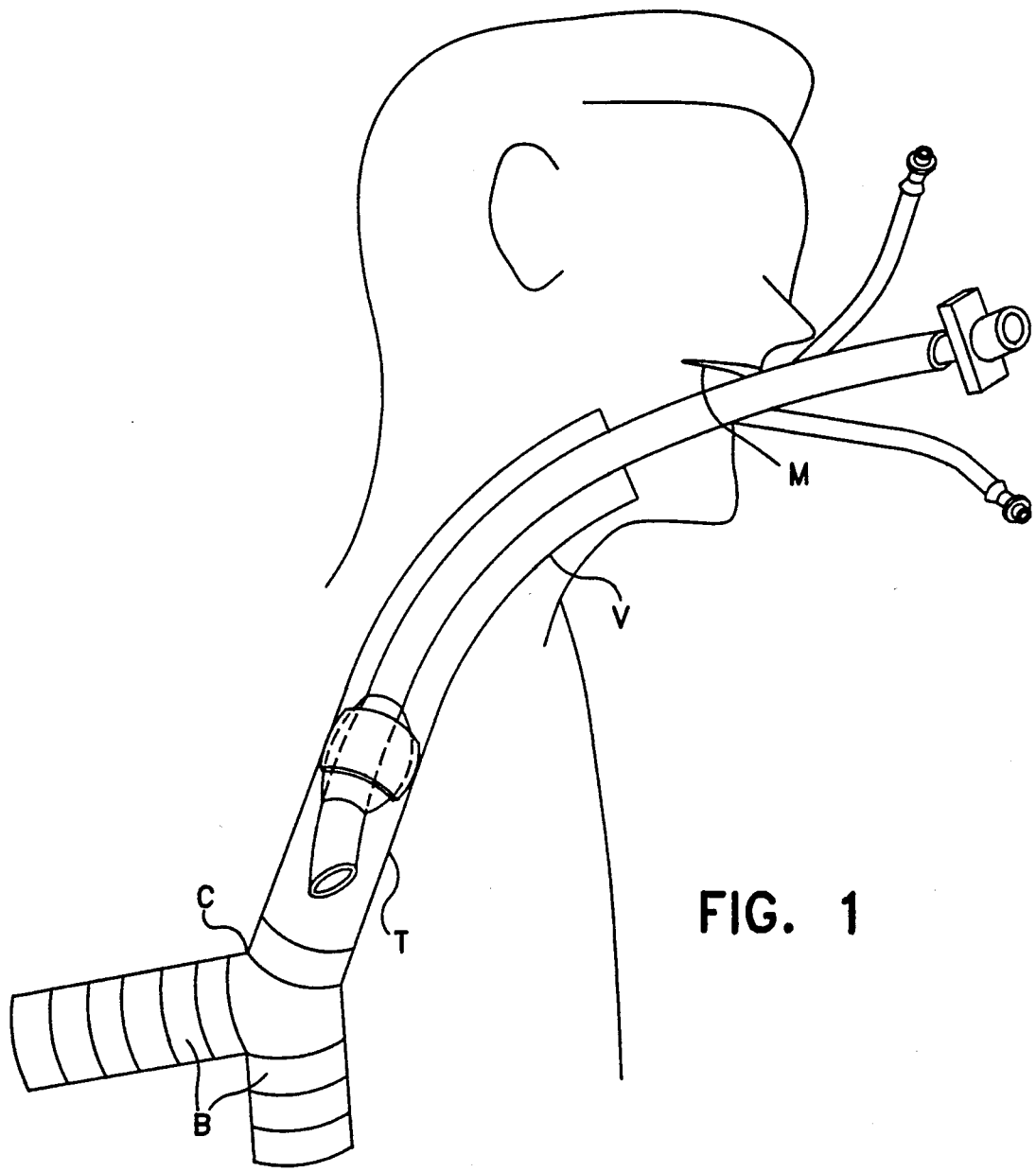
FIG. 1 is a perspective view of the endotracheal tube and related supply system for use on a patient.

View B illustrates an enlargement and expanded view of a focus b where intramural lumens of the endotracheal tube enter into cuffs.

DETAILED DESCRIPTION OF THE INVENTION

Although the invention is described in the following specifications with particular reference to the tracheal tonometry on cuffed endotracheal tube, the invention is equally applicable to simply constructed medical devices, such as cuffed tracheostomy tube or bronchial tube.

With reference to the drawings, wherein like numerals represent like parts throughout the figures, an endotracheal tube in accordance with the present invention is generally designated by the numeral 10 and the tonometry chamber by numeral 15.

Endotracheal tube 10 is adapted for insertion through the mouth M into the trachea T to facilitate mechanical ventilation as illustrated in FIG. 1. The tube 10 may be coupled to a ventilator (not shown) at its proximal end via tube connector 2.

The endotracheal tube 10 comprises a flexible ventilation tube 11 which extends from a tube connector 2 at a proximal end 3 to a distal end 16. The tube forms a primary ventilation passage 20 of substantially uniform diameter. The ventilation tube includes a linear segment of 11 extending from the distal end 16 therof.

The tube 10 is dimensioned to permit insertion through the mouth M and the trachea T of a patient in FIG. 1. The endotracheal tube 10 functions in a very efficient way to inhibit air leakage on inflation of the lungs. This is mainly achieved by a primary sealant cuff 13. The endotracheal tube is specifically adapted so that, upon intubation, the primary cuff 13 is located in the trachea T below the vocal cords V as illustrated in FIG. 1.

With reference to FIG. 3, the primary sealant cuff 13 comprises an inclusive inflatable balloon sleeve 12. The balloon sleeve 12 has opposing spaced reduced end 23 and 25 which seal against the tube wall 11 along cylindrical sleeve/pad interfaces to form a balloon sleeve which is inflatable and deflatable, as desired. In the deflated state(not illustrated) the balloon sleeve has a relatively smooth and uniform flattened surface to facilitate insertion into the patient. The surface of the sleeve 12 is perfectly soft and slippery. The primary sleeve 12 is diametrically dimensioned so that upon inflation, the sleeve expands circumferentially to seal against the tracheal wall of the patient below the vocal cord V. A lumen 22 formed in the the wall of the tube 11(in FIG. 3) has a port 30 distally which opens into the interior of the sleeve 12. This lumen is continuous proximally via tubing 5 with a syringe-controlled stop valve 4 for selectively inflating or deflating balloon sleeve. The tonometry cuff 15 is attached on the primary sealant cuff 13 in FIG. 2. The tonometry cuff 15 has an internal diameter which allows it to be fitted over the primary sealant cuff 13 on inflation and deflation. It also has enough tensile strength that it can be used as a balloon cuff during tonometry. Another characteristics of the tonometric cuff is that it can permeate carbon dioxide freely but not liquid. The preferred element of the tonometry cuff 13 is polydimethylsiloxane elastomer. The axial end segments of sleeve of tonometry cuff 14 are secured to the outer wall of the primary cuff 13 at the locations indicated by the reference numerals 26 and 28. The attachment may be made in any suitable fashion with adhesive being a suitable attachment medium. The material of the tubular element 14 possesse a characteristic whereby it is poorly permeable to liquid fluid while it is freely permeable to gas. The material is also substantially impermeable to the contents of tracheal or bronchial secretions. The lumen 24 which is formed in the wall of tube 11 as in illustration B-b of FIG. 3 is continuous distally via tract 18 to tonometry cuff 15. Proximally it is continuous via tubing 7 to the luer end lock 6, which is used for infusing or withdrawing the sample liquid for performing the tonometry. Preferrably the volume of the tonometry cuff 15 should be relatively small in order to facilitate rapid equilibration of gas yet it must be large enough so that a suitable sample of one milliliter for use in the gas analyzer can be withdrawn via the element 6. For example, around two milliliters is a favorable volume. The liquid media which will be filled in the tonometry cuff for tonometry is suitably normal saline. In a preferable way of operation, two milliliters of saline is filled in the tonometric cuff 15 via luer-cock end 6 and two milliliters of air is removed from the primary cuff 13. Thus the pressure exerted on the tracheal wall is unchanged during the tonometry. After 30 minutes, the saline is withdrawn from the tonometry cuff 15 via luer-cock end 6 and is subjected to regular blood gas analyzer(not shown). At the same time, the primary cuff 13 should be re-inflated with two milliliters of air to avoid any air leakage out of the ventilatory system.

A number of variations will become apparent without departing from the scope of the invention. For example, one such variation might be a tracheostomy tube with tonometry cuff on the primary sealant cuff. Another variation might be main tubular member which has plural primary cuffs with single or plural tonometry cuffs on the primary cuff(s).

What is claimed is:

1. A cuffed tracheal tube adapted for insertion through the mouth or tracheostomy site of a patient and into the patient's trachea comprising:
    an elongated tube means having a proximal end and a distal end portion, with said tube means defining a central ventilation passage;
    an inflatable primary sleeve means encircling said tube means between said proximal end and distal end for generally centrally locating and sealing the tube means in the trachea upon inflating thereof;
    second sleeve means located on said primary sleeve means and composed of a material that is freely permeable to carbon dioxide but poorly permeable to liquid or tracheo-bronchial contents for measuring the intramucosal partial pressure of carbon dioxide under said inflatable primary sleeve means;
    first means for selectively inflating and deflating said inflatable primary sleeve means; and,
    second means for infusing and withdrawing liquid from said second sleeve means whereby a liquid is transmitted into the said second sleeve means.

2. A method of monitoring the degree of ischemic injury of tracheal mucosa which comprises providing the cuffed tracheal tube of claim 1; infusing a volume of liquid into the second sleeve means; removing the same volume of air from the inflatable primary sleeve means; leaving the liquid in the second sleeve means for a sufficient length of time so that the carbon dioxide gas of the tracheal mucosa permeates across the second sleeve means and reaches equilibrium; withdrawing the liquid from the second sleeve means; analyzing the partial pressure of the carbon dioxide; withdrawing arterial blood and measuring the partial pressure of arterial carbon dioxide; and determining the presence and degree of ischemia on the basis of the difference between the arterial and tonometrically-derived carbon dioxide levels.

* * * * *